(12) United States Patent
Gorine et al.

(10) Patent No.: US 12,084,440 B2
(45) Date of Patent: Sep. 10, 2024

(54) POLYMORPH OF LATREPIRDINE DIHYDROCHLORIDE

(71) Applicant: Bigespas Ltd., London (GB)

(72) Inventors: Boris Gorine, Oakville (CA); Marina Yurovskaya, Moscow (RU)

(73) Assignee: BIGESPAS LTD., London (GB)

( * ) Notice: Subject to any disclaimer, the term of this patent is extended or adjusted under 35 U.S.C. 154(b) by 783 days.

(21) Appl. No.: 17/164,583

(22) Filed: Feb. 1, 2021

(65) Prior Publication Data

US 2022/0242860 A1   Aug. 4, 2022

(51) Int. Cl.
*C07D 471/04*   (2006.01)

(52) U.S. Cl.
CPC ........ *C07D 471/04* (2013.01); *C07B 2200/13* (2013.01)

(58) Field of Classification Search
CPC .......................... C07D 471/04; C07B 2200/13
See application file for complete search history.

(56) References Cited

U.S. PATENT DOCUMENTS

| | | |
|---|---|---|
| 6,187,785 B1 | 2/2001 | Zefirov et al. |
| 2007/0225316 A1 | 1/2007 | Bachurin et al. |

FOREIGN PATENT DOCUMENTS

WO   WO-2009111540 A1 *  9/2009   ........... C07D 471/04

OTHER PUBLICATIONS

Abramov. Y.A., Org. Process Res. Dev. 2013, 17, 472-485.

* cited by examiner

*Primary Examiner* — John S Kenyon
*Assistant Examiner* — Rehana Ismail
(74) *Attorney, Agent, or Firm* — McDonnell Boehnen Hulbert & Berghoff LLP

(57) ABSTRACT

The specification relates to a crystalline Latrepirdine dihydrochloride, Form DMB-I, method of its preparation, pharmaceutical composition containing it and its uses.

20 Claims, 1 Drawing Sheet

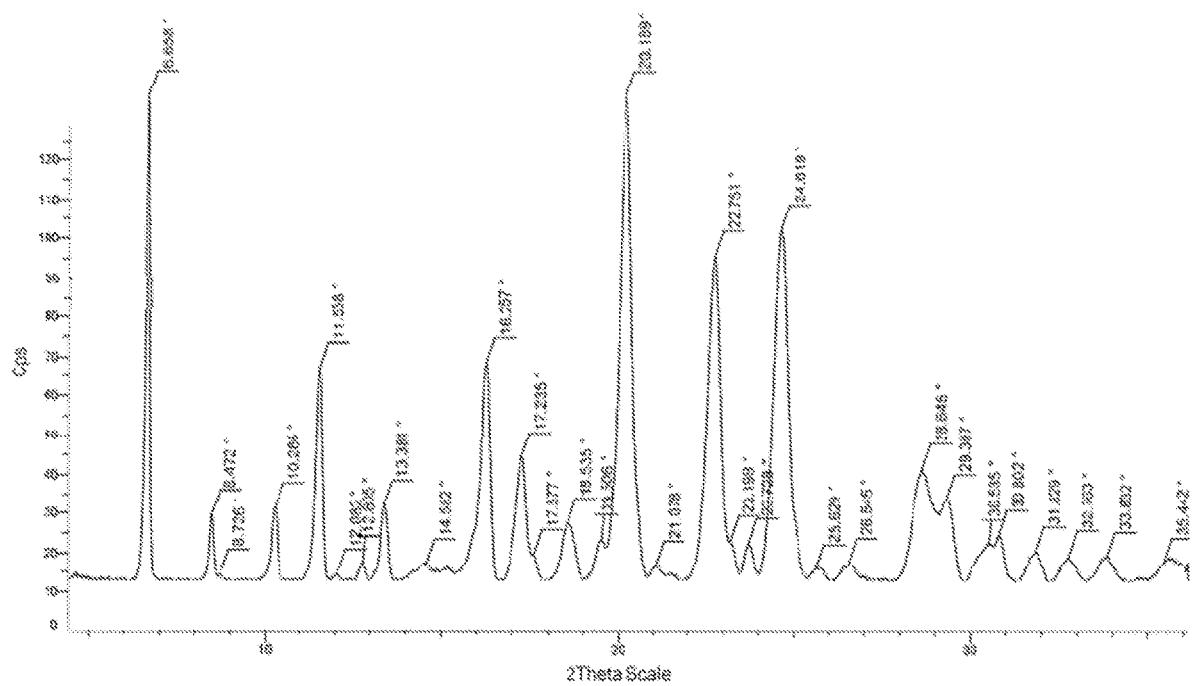

POLYMORPH OF LATREPIRDINE DIHYDROCHLORIDE

FIELD

The specification relates to a crystalline form of Latrepirdine and process for its preparation.

BACKGROUND

Pyridylethyl-substituted carboline compounds have been suggested for use in the treatment of various disorders, such as Alzheimer's disease, neurodegenerative disorders, and schizophrenia (see, for example, U.S. Pat. No. 6,187,785 and U.S. Pat. Appl. Pub. No. 2007/0225316, incorporated herein by reference).

The compound (2,8-dimethyl-5-[2-(6-methylpyridin-3-yl)ethyl]-3,4-dihydro-1H-pyrido[4,3-b]indole) (1), commonly known as Latrepirdine (Dimebon), is described in SU-01138164 and WO 2009/111540 A1 (both incorporated herein by reference), for instance, in Example 6. Latrepirdine was developed and marketed as an antihistamine agent and later was investigated for the treatment of Alzheimer's disease and Huntington chorea.

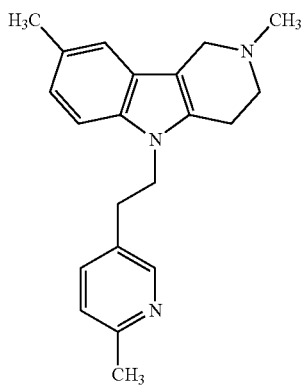

Crystalline forms of Latrepirdine, including anhydrous Form A, Form B hemi-hydrate, Form C monohydrate, Form D dihydrate, Form F trihydrate, and amorphous Latrepirdine dihydrochloride are reported in WO 2009/111540 A1 (incorporated herein by reference). However, these reported crystalline forms of Latrepirdine hydrochloride can be associated with various concerns, including hygroscopicity, poor crystallinity, poor crystalline homogeneity (i.e., mixtures of crystalline forms), the incorporation or use of toxic or questionable solvents for which no adequate safety data is available according to established ICH (International Council for Harmonisation of Technical Requirements for Pharmaceuticals for Human Use) guidelines, such as Q3C(R5), preparations that appear difficult to reproduce, or that can be impractical for commercial use.

In some cases, the use of alternative polymorphic forms of a drug substance can be useful in the development of a drug substance, such as Latrepirdine with preferred solubility profile, since polymorphism can directly alter the solubility and/or dissolution characteristics of the substance. Depending on the physicochemical characteristics of a new polymorph, such a form can be formulated to provide a drug product having enhanced solubility profile and potentially improved bioavailability. Furthermore, polymorphs having physicochemical attributes that are amenable to formulation processes, such as granulation and tabletting, can be formulated to provide drug products having higher dosage strength, allowing for the administration of fewer dose units daily.

Different crystalline forms of the same compound can have different packing, thermodynamic, spectroscopic, kinetic, surface and mechanical properties. For example, different crystalline forms may have different stability properties. A particular crystalline form may be more sensitive to heat, relative humidity (RH) and/or light. Alternatively, or additionally, a particular crystalline form may provide more compressibility and/or density properties thereby providing more desirable characteristics for formulation and/or product manufacturing. Particular crystalline forms may also have different dissolution rates, thereby providing different pharmacokinetic parameters, which allow for specific forms to be used in order to achieve specific pharmacokinetic targets. Differences in stability may result from changes in chemical reactivity, such as differential oxidation. Such properties may provide for more suitable product qualities, such as a dosage form that is more resistant to discolouration when comprised of a specific crystalline form. Different physical properties of crystalline forms may also affect their processing. For example, a particular crystalline form may be more resistant to flow, or may be more difficult to filter and/or wash.

Although general approaches to crystalline form screening of active pharmaceutical ingredients are known, it is well established that the prediction of whether any given compound will exhibit polymorphism is not possible. Furthermore, prediction of the properties of any unknown crystalline forms, and how they will differ from other crystalline forms of the same compound, remains even more elusive (Abramov. Y. A., Org. Process Res. Dev. 2013, 17, 472-485) (incorporated herein by reference). Therefore, there exists a need for novel crystalline forms of Latrepirdine for use in providing improved drug products containing Latrepirdine and their manufacture.

SUMMARY OF THE INVENTION

The crystalline Latrepirdine dihydrochloride, Form DMB-I, disclosed herein exhibits differences in properties when compared to the known crystalline forms of Latrepirdine. Properties that differ between the crystalline form disclosed herein and known crystalline forms of Latrepirdine include, for example: packing properties, such as, molar volume, density and hygroscopicity; thermodynamic properties, such as, melting point and solubility; kinetic properties, such as, dissolution rate and chemical/polymorphic stability; surface properties, such as, crystal habit; or mechanical properties, such as, hardness, tensile strength, compactibility, tabletting, handling, flowability, and blending.

In one aspect, the specification relates to a crystalline Latrepirdine dihydrochloride, Form DMB-I, which has a powder X-ray diffraction (PXRD) pattern having peaks, expressed in degrees 2θ (±0.2°), at 6.7°, 8.5°, 10.3°, and 11.6°.

In on embodiment, the specification relates to a crystalline Latrepirdine dihydrochloride, Form DMB-I, which has a powder X-ray diffraction (PXRD) pattern having at least four peaks, expressed in degrees 2θ (±0.2°), wherein the peaks are at: 12.8°, 13.4°, 16.3°, 17.2°, 20.2°, 22.8°, 24.6°, 28.6° or 29.3°. In another embodiment, the specification relates to a crystalline Latrepirdine dihydrochloride, Form DMB-I, which has a powder X-ray diffraction (PXRD) pattern having peaks, expressed in degrees 2θ (±0.2°), at 12.8°, 13.4°, 16.30, 17.20, 20.20, 22.80, 24.60, 28.60 and 29.30.

In another aspect, the specification relates to a crystalline Latrepirdine dihydrochloride, Form DMB-I, which has a powder X-ray diffraction (PXRD) pattern having peaks, expressed in degrees 2θ (±0.2°), at 6.7°, 11.6°, 16.3°, 20.2°, 22.8° and 24.6°. In one embodiment, the specification relates to a crystalline Latrepirdine dihydrochloride, Form DMB-I, which has a powder X-ray diffraction (PXRD) pattern having peaks, expressed in degrees 2θ (±0.2°), at 17.2° and 28.60.

In a further aspect, the specification relates to a crystalline Latrepirdine dihydrochloride, Form DMB-I, corresponding substantially to the representative powder X-ray diffraction (PXRD) pattern as shown FIG. 1.

In still another aspect, the specification relates to a pharmaceutical composition containing the crystalline Latrepirdine dihydrochloride, Form DMB-I, as disclosed herein.

In a still further aspect, the specification relates to a method of treatment and/or prevention of a neurodegenerative or other disease or as an antihistamine, by use of the crystalline Latrepirdine dihydrochloride, Form DMB-I, or pharmaceutical composition containing crystalline Latrepirdine dihydrochloride, Form DMB-I, as disclosed herein.

In another further aspect, the specification relates to a process for preparation of a crystalline Latrepirdine dihydrochloride, Form DMB-I, the process containing the steps of:
dissolving Latrepirdine free base in a solvent, wherein the solvent is an aliphatic alcohol;
sparging the solution containing the Latrepirdine free base in the solvent with gaseous hydrogen chloride;
adding an anti-solvent, wherein the anti-solvent is an aliphatic ether, and
collecting the crystalline Latrepirdine dihydrochloride, Form DMB-I, by filtration.

BRIEF DESCRIPTION OF THE DRAWINGS

Reference will now be made, by way of example, to the accompanying drawings which show example embodiments of the present application, and in which:

FIG. 1 is a representative powder X-ray diffraction (PXRD) diffractogram of Latrepirdine dihydrochloride Form DMB-I, in accordance with the specification.

DESCRIPTION OF EXAMPLE EMBODIMENTS

The specification may be understood more readily by reference to the following detailed description and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, the term "about" means within a statistically meaningful range of a value, such as a stated concentration range, time frame, molecular weight, particle size, temperature or pH. Such a range can be within an order of magnitude, typically within 20%, more typically within 10%, and even more typically within 5% of the indicated value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

The specification relates to a crystalline form of Latrepirdine that can provide improved properties when compared to known crystalline forms of Latrepirdine. Properties that differ between the crystalline form of Latrepirdine, disclosed herein, and the known crystalline forms of Latrepirdine include: packing properties, such as, molar volume, density and hygroscopicity; thermodynamic properties, such as, melting point and solubility; kinetic properties, such as, dissolution rate and chemical/polymorphic stability; surface properties, such as, crystal habit; and mechanical properties, such as, hardness, tensile strength, compactibility, tableting, handling, flowability, and blending. Furthermore, the crystalline form of Latrepirdine, disclosed herein, may be prepared by facile and industrially advantageous processes when compared to the crystalline forms of Latrepirdine known in the art. The properties provided by the crystalline form Latrepirdine, disclosed herein, can provide practical advantages over known forms of Latrepirdine, and can be exploited to meet specific needs in the manufacture and formulation of Latrepirdine.

In one aspect, the specification relates to a crystalline Latrepirdine dihydrochloride, Form DMB-I, which has a powder X-ray diffraction (PXRD) pattern having peaks, expressed in degrees 2θ (±0.2°), at 6.7°, 8.5°, 10.3°, and 11.6°. In one embodiment, for example and without limitation, the specification relates to a crystalline form of Latrepirdine, Latrepirdine Dihydrochloride Form DMB-I. In another embodiment, for example and without limitation, Form DMB-I is unsolvated. In another embodiment, for example and without limitation, Form DMB-I is anhydrous and unsolvated.

The terms, 'crystalline form', 'crystal', 'crystalline' and the like, as used herein are not particularly limited, and should be known to a person of skill in the art. In one embodiment, for example and without limitation, the terms refer to a substance with a particular arrangement of molecular components in its crystal lattice, and which may be identified by physical characterization methods, such as, for example and without limitation, PXRD.

The term, 'solvate' and 'unsolvated' as used herein, is not particularly limited and should be known to a person of skill in the art. In one embodiment, for example and without limitation, solvate refers to a crystal form of a substance which contains solvent. As such, the term, 'unsolvated' refers to a crystal form of a substance that is generally free of, substantially free of or without solvent.

The term, 'anhydrous' as used herein is not particularly limited and should be known to a person of skill in the art. In one embodiment, for example and without limitation, anhydrous relates to a substance, or with reference to the crystalline Latrepirdine dihydrochloride Form DMB-I disclosed herein, a crystalline compound, that contains no water, or substantially free of water.

The term, 'Powder X-ray Diffraction', 'PXRD', or the like are not particularly limited and should be known to a person of skill in the art, who should recognize that PXRD is a scientific technique using X-ray on powder or microcrystalline samples for structural characterization of materials.

In addition, differences in PXRD patterns among separate measurements of the same polymorph may arise for many reasons. For instance, sources of error include variations in sample preparation (e.g. sample height), instrument errors, calibration errors, and operator errors (including errors in determining peak locations). Preferential orientation, i.e., a lack of random orientation of crystals in the PXRD sample, can result in significant differences in relative peak heights. Calibration errors and sample height errors often result in a shift of all of the peaks of the diffractogram in the same direction and by the same amount. Small differences in sample height on a flat holder may lead to large displacements in PXRD peak positions. For a systematic study showing that sample height differences of 1 mm may lead to peak shifts as high as 1° 2θ, see Chen et al., *J. Pharmaceutical and Biomedical Analysis* (2001) 26:63 (incorporated herein by reference).

In many instances, peak shifts among diffraction patterns resulting from systematic error can be eliminated by compensating for the shift (e.g., applying a correction factor to all peak position values) or by recalibrating the diffractometer. Generally, same techniques can be used to compensate for differences among diffractometers so that PXRD peak positions obtained from two different instruments can be brought into agreement. Furthermore, when these techniques are applied to PXRD measurements from the same or different diffractometers, the peak positions for a particular polymorph will usually agree to within about ±0.2° 2θ.

As noted above, the specification relates to Latrepirdine Dihydrochloride Form DMB-I, characterized by a powder X-ray diffraction (PXRD) diffractogram having peaks, expressed in degrees 2θ (±0.2°), at 6.7°, 8.5°, 10.3° and 11.6°. In one embodiment, for example and without limitation, the PXRD diffractogram further contains at least four peaks, expressed in degrees 2θ (±0.2°), selected from the group consisting of: 12.8°, 13.4°, 16.3°, 17.2°, 20.2°, 22.8°, 24.6°, 28.6° and 29.3°. In another embodiment, for example and without limitation, the PXRD diffractogram further contains peaks, expressed in degrees 2θ (±0.20), at 12.80, 13.40, 16.30, 17.20, 20.20, 22.80, 24.60, 28.60 and 29.30. An illustrative PXRD diffractogram of Latrepirdine Form DMB-I, as prepared in Example 1, is shown in FIG. 1.

As such, in a further embodiment, for example and without limitation, the specification relates to crystalline Latrepirdine dihydrochloride, Form DMB-I, having essentially the same PXRD pattern as shown in FIG. 1.

As used herein, the term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2° or 0.1°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. As such, although illustrative of the PXRD diffractogram that is provided for the Latrepirdine Form DMB-I, disclosed herein, the relative intensities of the peaks are variable. Thus, depending on a particular sample, the prominence or relative intensity of the peaks observed may differ from those in the illustrative PXRD diffractogram and peak listing, as mentioned above.

A peak listing, comprising representative peaks from the PXRD diffractogram in FIG. 1, and their relative intensities, is provided in Table 1.

TABLE 1

Relative peak intensities of Latrepirdine Dihydrochloride Form DMB-I from FIG. 1.

| Angle (°, 2θ) | Relative intensity (%) |
|---|---|
| 6.66 | 100.0 |
| 8.47 | 13.6 |
| 10.29 | 15.2 |
| 11.56 | 44.0 |
| 12.80 | 4.2 |
| 13.38 | 15.8 |
| 16.26 | 44.9 |
| 17.24 | 25.5 |
| 20.19 | 99.8 |
| 22.75 | 66.9 |
| 24.62 | 72.5 |
| 28.64 | 23.2 |
| 29.31 | 17.0 |

In another further aspect, the specification relates to a process for preparation of a crystalline Latrepirdine dihydrochloride, Form DMB-I, the process containing the steps of:

dissolving Latrepirdine free base in a solvent to form a solution, wherein the solvent is an aliphatic alcohol;

sparging or bubbling the solution with gaseous hydrogen chloride;

adding an anti-solvent, wherein the anti-solvent is an aliphatic ether, and collecting the crystalline Latrepirdine dihydrochloride, Form DMB-I, by filtration.

The step of dissolving Latrepirdine free base is not particularly limited and can be varied. In one embodiment, parameters that can be varied can include, for example and without limitation, ratio of volume or weight of solvent to the weight of Latrepirdine free base, temperature for carrying out the step of dissolution, agitation rate and time for dissolution.

In one embodiment, for example and without limitation, the ratio of weight of Latrepirdine free base to the volume of solvent is from about 1 g/5 ml to about 1 g/20 ml, and all values in between. In a particular embodiment, for example and without limitation, the ratio of weight of Latrepirdine free base to the volume of solvent is about 1 g/8 ml, about 1 g/9 ml, about 1 g/10 ml, about 1 g/11 ml, about 1 g/12 ml, about 1 g/13 ml, about 1 g/14 ml or about 1 g/15 ml.

In another embodiment, for example and without limitation, the dissolution or dissolving of Latrepirdine free base is carried out at from a low temperature to a high temperature. In a particular embodiment, the temperature for carrying out the step of dissolution is from about 5° C. to about 60° C., and all values in between. In another particular embodiment, for example and without limitation, the temperature for carrying out the step of dissolution is about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C. or about 40° C.

In a further embodiment, for example and without limitation, after dissolving Latrepirdine free base in the solvent to form a solution, the solution can be cooled to attain an internal temperature before and during addition of the hydrogen chloride gas. The internal temperature so attained and/or maintained is not particularly limited and can be determined. In one embodiment, the internal temperature so attained and/or maintained is, for example and without limitation, from about 10° C. to about 40° C., and all values in between. In another embodiment, for example and without limitation, the internal temperature so attained and/or maintained is 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C. or 35° C.

In still another embodiment, for example and without limitation, agitation rate and time for dissolution can be varied to dissolve Latrepirdine free base in the solvent. In a particular embodiment, Latrepirdine free base can be agitated in the solvent for, for example and without limitation, about 30 minutes to 4 hours. In a further embodiment, for example and without limitation, Latrepirdine free base can be agitated in the solvent for about 45 min., about 50 min., about 55 min., about 60 min., about 70 min., about 80 min., about 90 min., about 100 min., about 110 min. or about 120 min.

The term 'aliphatic alcohol' as used herein is not particularly limited and should be known to a person of skill in the art. In addition, the aliphatic alcohol used for dissolving the Latrepirdine free base is not particularly limited and can be determined. Aliphatic alcohols include an organic compound having an alcohol (—OH) functional group, where the aliphatic chain contains carbon and hydrogen joined together in straight chain, branched chain, or non-aromatic rings. Further, the length of the aliphatic chain is not particularly limited. In one embodiment, the aliphatic alcohol used for dissolving Latrepirdine free is, for example and without limitation, methanol, ethanol, propanol, isopropanol, 1-butanol, 2-butanol, iso-butanol, tert-butanol, 1-pentanol, 2-pentanol, 3-pentanol, 2-methyl-1-butanol, 3-methyl-1-butanol, 2,2-dimethyl-1-propanol, 3-methyl-2-butanol or 2-methyl-2-butanol, or combinations thereof. In a particular embodiment, for example and without limitation, the aliphatic alcohol used for dissolving Latrepirdine free is methanol or ethanol.

The step of sparging or bubbling hydrogen chloride (HCl) gas in the solution containing Latrepirdine free is not particularly limited. In one embodiment, for example and without limitation, the rate of bubbling, time and temperature of the solution can be varied depending upon experimental and equipment design. In a particular embodiment, for example and without limitation, HCl gas is bubbled in the solution, containing the Latrepirdine free base, for a sufficient time to attain saturation of the solution with HCl gas. In a further embodiment, for example and without limitation, during the addition of the HCl gas, the internal temperature of the solution, containing the Latrepirdine free base, is maintained as described herein.

The step of adding an anti-solvent after addition of HCl gas to the solution, containing the Latrepirdine free base, is not particularly limited. In one embodiment, parameters that can be varied can include, for example and without limitation, types of anti-solvent, ratio of volume of anti-solvent to volume of solvent, temperature for addition of anti-solvent, agitation rate and time for agitation.

In one embodiment, the anti-solvent is, for example and without limitation, an aliphatic ether. The aliphatic ether used is not particularly limited. In one embodiment, for example and without limitation, the aliphatic ether is tert-amyl ethyl ether, cyclopentyl methyl ether, di-tert-butyl ether, di(propylene glycol) methyl ether, dibutyl ether, diethyl ether, diisopropyl ether, dimethoxyethane, dimethoxymethane, 1,4-dioxane, ethyl tert-butyl ether, methoxyethane, 2-(2-methoxyethoxy)ethanol, methyl tert-butyl ether, 2-methyltetrahydrofuran, propylene glycol methyl ether, tetrahydrofuran, tetrahydrofurfuryl alcohol, tetrahydropyran or 2,2,5,5-tetramethyltetrahydrofuran. In a particular embodiment, for example and without limitation, the anti-solvent is diethyl ether.

The volume of anti-solvent added is not particularly limited, and can be varied depending upon the solvent and anti-solvent used. In one embodiment, for example and without limitation, the solvent is ethanol and the anti-solvent is diethyl ether.

The ratio of volume of anti-solvent to volume of solvent is also not particularly limited and can be varied depending upon experimental and apparatus design requirements. In one embodiment, the ratio of volume of anti-solvent to volume of solvent is, for example and without limitation, about 3:1, 2.5:1, 2:1, 1.5:1, 1:1, 1:1.5, 1:2, 1:2.5 or 1:3. In a particular embodiment, for example and without limitation, the anti-solvent is diethyl ether and the solvent is ethanol, and the ratio of the volume of anti-solvent to the volume of solvent is 1:1.

The agitation rate and time for agitation is not particularly limited and can be varied. In one embodiment, for example and without limitation, upon precipitation of Latrepirdine dihydrochloride, the suspension or slurry can be agitated from about 30 minutes to 4 hours. In a further embodiment, for example and without limitation, the slurry can be agitated for about 45 min., about 50 min., about 55 min., about 60 min., about 70 min., about 80 min., about 90 min., about 100 min., about 110 min. or about 120 min.

In a further embodiment, for example and without limitation, the temperature after addition of the anti-solvent can be maintained or reduced to affect the precipitation of Latrepirdine dihydrochloride. The temperature so attained and/or maintained is not particularly limited and can be determined. In one embodiment, the internal temperature so attained and/or maintained is, for example and without limitation, from about 10° C. to about 35° C., and all values in between. In another embodiment, for example and without limitation, the internal temperature so attained and/or maintained is 15° C., 16° C., 17° C., 18° C., 19° C., 20° C., 21° C., 22° C., 23° C., 24° C., 25° C., 26° C., 27° C., 28° C., 29° C. or 30° C.

After formation of the crystalline Latrepirdine dihydrochloride, Form DMB-I, the crystals can be collected by filtration. The method of filtration is not particularly limited and can varied, depending upon experiment design and equipment requirements. Methods of filtration should be known to a person of skill in the art.

As described in Example 1, Latrepirdine Form DMB-I is prepared by saturating a solution of Latrepirdine free base in 10 volume parts of ethanol with gaseous hydrogen chloride while maintaining the temperature below 20-30° C. followed by addition of 10 volume parts of diethyl ether. Filtration of the resulting suspension provides Latrepirdine Form DMB-I having a PXRD diffractogram consistent with that of FIG. 1.

The present specification also relates to pharmaceutical compositions comprising the crystalline Latrepirdine dihydrochloride, Form DMB-I, disclosed herein. Pharmaceutical compositions of the present invention are not particularly limited and may, for example, be in a form suitable for oral administration as a tablet, capsule, pill, powder, sustained release formulations, solution, suspension, for parenteral injection as a sterile solution, suspension or emulsion, or for rectal administration as a suppository. The pharmaceutical composition may be in unit dosage forms suitable for single administration of precise dosages. The pharmaceutical composition include a conventional pharmaceutical carrier or excipient and the crystalline Latrepirdine dihydrochloride, Form DMB-I, disclosed herein, as an active ingredient. In addition, it may include other medicinal or pharmaceutical agents, carriers, adjuvants, etc.

Suitable pharmaceutical excipient or carriers include inert diluents or fillers, water and various organic solvents. The pharmaceutical compositions may, if desired, contain additional ingredients such as flavorings, binders, excipients and the like. Thus for oral administration, tablets containing various excipients may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Additional materials can include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975) (incorporated herein by reference).

The phrase "pharmaceutically acceptable" refers to substances, which are within the scope of sound medical judgment, suitable for use in contact with the tissues of patients without undue toxicity, irritation, allergic response, and the like, commensurate with a reasonable benefit/risk ratio, and effective for their intended use.

The crystalline Latrepirdine dihydrochloride, Form DMB-I, disclosed herein, or the pharmaceutical composition containing it, can find use in the treatment and/or prevention of a neurodegenerative or other disease or may find use as an antihistamine. For instance, crystalline Latrepirdine dihydrochloride, Form DMB-I, detailed herein, may be used in the treatment and/or prevention of Alzheimer's disease, Huntington's disease, canine cognitive dysfunction syndrome, ALS, schizophrenia, ischemia/reperfusion injury of the brain, mild cognitive impairment and in methods of slowing aging in a mammal or methods of slowing the aging of a cell, tissue, or organ. They may be administered alone or in combination with other active agents.

EXAMPLES

The following non-limiting examples are illustrative of some of the aspects and embodiments of the invention described herein.

The Latrepirdine free base used as a starting material in the following examples was consistent with Latrepirdine which is reported in WO 2009/111540 A1 (Examples 4 and 6).

Powder X-Ray Diffraction Analysis

PXRD data were acquired on Bruker D8 Discover diffractometer equipped with a copper source (1.54060 Å) and Eiger 2R-500K (2 Dimensional) detector with operational voltage and amperage set to 50.0 kV and 1000.0 μA, respectively. Diffraction pattern was acquired using step size of 0.01° 2θ over a range of 4.5-36° 2θ with total time of 180 s. Data were collected in Bragg-Brentano geometry, using compact sample placed under Kapton film.

Example 1: Preparation of Latrepirdine Dihydrochloride Form DMB-I

A suspension of Latrepirdine free base (100 g) in anhydrous ethanol (1000 ml) was agitated at 15-20° C. for approximately 1 hour to afford a solution. The solution was cooled to 15-20° C. using external cooling bath and the stream of hydrogen chloride was sparged into solution until saturation while maintaining internal temperature below 20-30° C. Diethyl ether (1000 mL) was added gradually with agitation. A suspension that formed was agitated for an additional 30 minutes and then filtered and washed forward with 200 ml of diethyl ether. The filter cake was pulled dry under a nitrogen to afford 112 g (91%) of Latrepirdine Dihydrochloride Form DMB-I as a white, free flowing solid with M. P.=205-206° C. The PXRD diffractogram of a sample prepared by this process is shown in FIG. 1. 1H-NMR (d6-DMSO) δ=11.52 (br s, 1H), 8.55 (s, 1H), 8.21 (d, J=6 Hz, 1H), 7.73 (d, J=6 Hz, 1H), 7.37 (d, J=6 Hz, 1H), 7.20 (s, 1H), 6.95 (d, J=6 Hz, 1H), 4.39 (m, 3H), 4.19 (m, 1H) 3.07-3.70 (m, 6H), 2.91 (d, J=1 Hz, 3H), 2.68 (s, 3H) 2.37 (s, 3H).

Certain adaptations and modifications of the described embodiments can be made. Therefore, the above discussed embodiments are considered to be illustrative and not restrictive.

What is claimed is:

1. A crystalline Latrepirdine dihydrochloride, Form DMB-I, which has a powder X-ray diffraction (PXRD) pattern having peaks, expressed in degrees 2θ (±0.2°), at 6.7°, 8.5°, 10.3°, and 11.6°.

2. The crystalline Latrepirdine dihydrochloride, Form DMB-I, according to claim 1, which has a powder X-ray diffraction (PXRD) pattern having at least four peaks, expressed in degrees 2θ (±0.2°), wherein the peaks are: 12.8°, 13.4°, 16.3°, 17.2°, 20.2°, 22.8°, 24.6°, 28.6° or 29.3°.

3. The crystalline Latrepirdine dihydrochloride, Form DMB-I, according to claim 1, which has a powder X-ray diffraction (PXRD) pattern having peaks, expressed in degrees 2θ (±0.2°), at 12.8°, 13.4°, 16.3°, 17.2°, 20.2°, 22.8°, 24.6°, 28.6° and 29.3°.

4. The crystalline Latrepirdine dihydrochloride, Form DMB-I, according to claim 1, which has a powder X-ray diffraction (PXRD) pattern having the following peaks, expressed in degrees 2θ (±0.2°):

| Peak | 2θ (±0.2°) |
|---|---|
| 1 | 6.66 |
| 2 | 8.47 |
| 3 | 10.29 |
| 4 | 11.56 |
| 5 | 12.80 |
| 6 | 13.38 |
| 7 | 16.26 |
| 8 | 17.24 |
| 9 | 20.19 |
| 10 | 22.75 |
| 11 | 24.62 |
| 12 | 28.64 |
| 13 | 29.31. |

5. The crystalline Latrepirdine dihydrochloride, Form DMB-I, according to claim 1, corresponding to the representative powder X-ray diffraction (PXRD) pattern as shown FIG. 1.

6. A pharmaceutical composition comprising crystalline Latrepirdine dihydrochloride, Form DMB-I, and a pharmaceutically acceptable excipient, wherein the crystalline Latrepirdine dihydrochloride, Form DMB-I, has a powder X-ray diffraction (PXRD) pattern having peaks, expressed in degrees 2θ (±0.2°), at 6.7°, 8.5°, 10.3°, and 11.6°.

7. The pharmaceutical composition of claim 6, wherein the crystalline Latrepirdine dihydrochloride, Form DMB-I, has a powder X-ray diffraction (PXRD) pattern having at least four peaks, expressed in degrees 2θ (±0.2°), wherein the peaks are: 12.8°, 13.4°, 16.3°, 17.2°, 20.2°, 22.8°, 24.6°, 28.6° or 29.3°.

8. The pharmaceutical composition of claim 6, wherein the crystalline Latrepirdine dihydrochloride, Form DMB-I, has a powder X-ray diffraction (PXRD) pattern having peaks, expressed in degrees 2θ (±0.2°), at: 12.8°, 13.4°, 16.3°, 17.2°, 20.2°, 22.8°, 24.6°, 28.6° and 29.3°.

9. The pharmaceutical composition of claim 6, wherein the crystalline Latrepirdine dihydrochloride, Form DMB-I, has a powder X-ray diffraction (PXRD) pattern having the following peaks, expressed in degrees 2θ (±0.2°):

| Peak | 2θ (±0.2°) |
|---|---|
| 1 | 6.66 |
| 2 | 8.47 |
| 3 | 10.29 |
| 4 | 11.56 |
| 5 | 12.80 |
| 6 | 13.38 |
| 7 | 16.26 |
| 8 | 17.24 |
| 9 | 20.19 |
| 10 | 22.75 |
| 11 | 24.62 |
| 12 | 28.64 |
| 13 | 29.31. |

10. A method of treatment and/or prevention of a neurodegenerative or other disease or as an antihistamine, comprising administrating the crystalline Latrepirdine dihydrochloride, Form DMB-I, according to claim 1.

11. A method of treatment and/or prevention of a neurodegenerative or other disease or as an antihistamine, comprising administrating the crystalline Latrepirdine dihydrochloride, Form DMB-I, according to claim 2.

12. A method of treatment and/or prevention of a neurodegenerative or other disease or as an antihistamine, comprising administrating the crystalline Latrepirdine dihydrochloride, Form DMB-I, according to claim 3.

13. A method of treatment and/or prevention of a neurodegenerative or other disease or as an antihistamine, comprising administrating the pharmaceutical composition containing crystalline Latrepirdine dihydrochloride, Form DMB-I, according to claim 6.

14. A method of treatment and/or prevention of a neurodegenerative or other disease or as an antihistamine, comprising administrating the pharmaceutical composition containing crystalline Latrepirdine dihydrochloride, Form DMB-I, according to claim 7.

15. A method of treatment and/or prevention of a neurodegenerative or other disease or as an antihistamine, comprising administrating the pharmaceutical composition containing crystalline Latrepirdine dihydrochloride, Form DMB-I, according to claim 8.

16. A process for preparation of a crystalline Latrepirdine dihydrochloride, Form DMB-I, the process comprising the steps of:
dissolving Latrepirdine free base in a solvent, wherein the solvent is an aliphatic alcohol;
bubbling the solution containing the Latrepirdine free base in the solvent with gaseous hydrogen chloride;
adding an anti-solvent, wherein the anti-solvent is an aliphatic ether, and
collecting the crystalline Latrepirdine dihydrochloride, Form DMB-I, by filtration.

17. The process according to claim 16, wherein the step of bubbling the solution with gaseous hydrogen chloride is carried out while maintaining the solution temperature below 20-30° C.

18. The process according to claim 16, wherein the solvent for dissolving the free base of latrepirdine is ethanol.

19. The process according to claim 16, wherein the anti-solvent is diethyl ether.

20. The process according to claim 16, wherein the ratio of volume of anti-solvent to volume of solvent is 1:1.

* * * * *